(12) United States Patent
Lassoued et al.

(10) Patent No.: US 11,355,241 B2
(45) Date of Patent: Jun. 7, 2022

(54) INTELLIGENT HEALTH RECOMMENDATION SERVICE

(71) Applicant: INTERNATIONAL BUSINESS MACHINES CORPORATION, Armonk, NY (US)

(72) Inventors: Yassine Lassoued, Dublin (IE); Julien Monteil, Dublin (IE); Joao H. Bettencourt-Silva, Dublin (IE); Giovanni Russo, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 713 days.

(21) Appl. No.: 16/201,512

(22) Filed: Nov. 27, 2018

(65) Prior Publication Data
US 2020/0168335 A1    May 28, 2020

(51) Int. Cl.
*G16H 50/20*    (2018.01)
*G06N 20/00*    (2019.01)
*G16H 50/30*    (2018.01)

(52) U.S. Cl.
CPC ............ *G16H 50/20* (2018.01); *G06N 20/00* (2019.01); *G16H 50/30* (2018.01)

(58) Field of Classification Search
CPC ......... G16H 50/20; G16H 50/30; G06N 20/00
See application file for complete search history.

(56) References Cited

U.S. PATENT DOCUMENTS

| | | | |
|---|---|---|---|
| 6,809,643 B1 | 10/2004 | Elrod et al. | |
| 8,725,311 B1 | 5/2014 | Breed | |
| 9,122,775 B2 | 9/2015 | Schunder et al. | |
| 10,346,697 B2 * | 7/2019 | Adibi | B60K 28/066 |
| 2001/0011224 A1 | 8/2001 | Brown | |
| 2008/0086318 A1 | 4/2008 | Gilley et al. | |
| 2014/0244296 A1 | 8/2014 | Linn et al. | |
| 2015/0088538 A1 | 3/2015 | Dykes et al. | |
| 2016/0342906 A1 * | 11/2016 | Shaashua | H04W 4/029 |
| 2017/0151957 A1 | 6/2017 | Boesen | |
| 2017/0216518 A1 * | 8/2017 | Davis | G16H 50/70 |
| 2017/0232326 A1 | 8/2017 | Gilley et al. | |

(Continued)

OTHER PUBLICATIONS

S. Asthana, A. Megahed and R. Strong, "A Recommendation System for Proactive Health Monitoring Using IoT and Wearable Technologies," 2017 IEEE International Conference on AI & Mobile Services (AIMS), 2017, pp. 14-21, doi: 10.1109/AIMS.2017.11. (Year: 2017).*

(Continued)

*Primary Examiner* — Evangeline Barr
(74) *Attorney, Agent, or Firm* — Griffiths & Seaton PLLC

(57) ABSTRACT

Embodiments for implementing an intelligent health recommendation service by a processor. A health state of a user may be learned according to user behavior, physical conditions of the user, activities of daily living (ADL) and associated context of daily living (CDL) of the user, or a combination thereof. One or more applications, one or more application components, one or more internet of things (IoT) devices, or a combination thereof may be identified and recommended to minimize one or more possible negative impacts upon the health state of the user.

20 Claims, 7 Drawing Sheets

(56) References Cited

U.S. PATENT DOCUMENTS

2018/0001184 A1* 1/2018 Tran .................. G06F 1/163

OTHER PUBLICATIONS

J. S. Dhillon, B. C. Wünsche and C. Lutteroth, "Accessible telehealth—Leveraging consumer-level technologies and social networking functionalities for senior care," 2013 6th International Conference on Human System Interactions (HSI), 2013, pp. 451-458, doi: 10.1109/HSI.2013.6577864. (Year: 2013).*

* cited by examiner

INTELLIGENT HEALTH RECOMMENDATION SERVICE

BACKGROUND OF THE INVENTION

Field of the Invention

The present invention relates in general to computing systems, and more particularly to, various embodiments for implementing an intelligent health recommendation service by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize and mitigate adverse impacts on a well-being or health of a person.

SUMMARY OF THE INVENTION

Various embodiments for implementing an intelligent health recommendation service/assistant using one or more processors, are provided. In one embodiment, by way of example only, a method for implementing an intelligent health recommendation service, again by a processor, is provided. A health state of a user may be learned according to user behavior, physical conditions of the user, activities of daily living (ADL) and associated context of daily living (CDL) of the user, or a combination thereof. One or more applications, one or more application components, one or more internet of things (IoT) devices, or a combination thereof may be identified and recommended to minimize one or more possible negative impacts upon the health state of the user.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
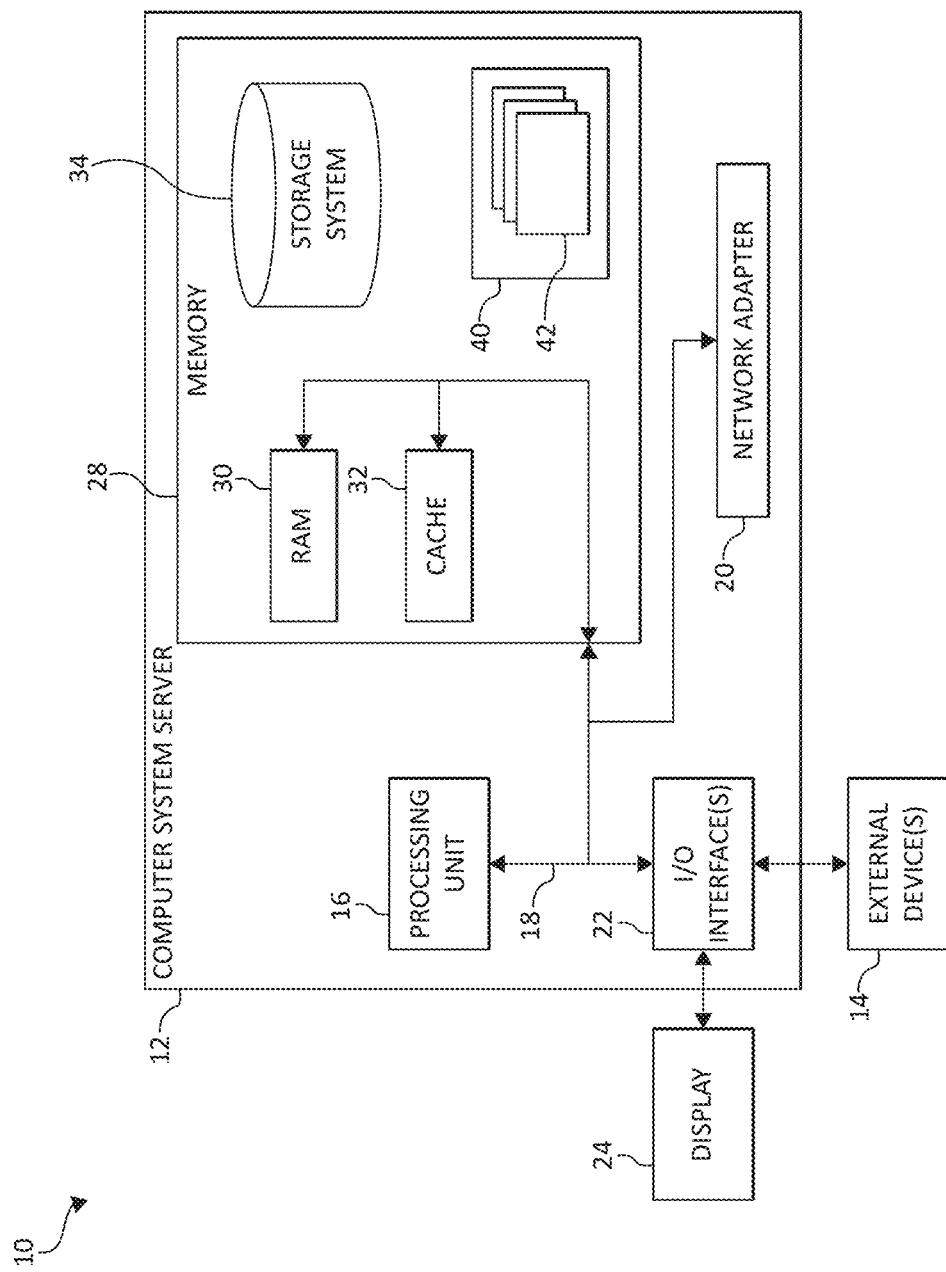
FIG. 1 is a block diagram depicting an exemplary computing node according to an embodiment of the present invention.

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices," which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user. For example, as the demand for and access to data continues to expand in society, consumers of information content, particularly individuals desiring to make well-informed decisions regarding a medical condition or health state, continue to increase. The openness of the internet with the ever-increasing availability of a variety of types of computing devices, IoT devices, and the cloud computing environment for viewing, interacting, or engaging with information, provides the ability of users to have continuous access to information content relating to a variety of settings. For example, there is a growing interest in personal health applications and recommender systems. However, current systems fall within one of the following categories: 1) devices and applications dedicated to only specific health condition or activities, (e.g., diabetes monitors, fitness trackers, etc.), 2) general companions that may assist users to diagnose their health conditions via dialogue, and/or 3) health recommender systems that recommend health products (e.g., medicine, reading material, etc.). These approaches do not provide a generic solution for a personalized health companion suitable for various health conditions and makes use of a flexible set of health devices.

Accordingly, the present invention provides for implementing an intelligent health recommendation service by a processor. A health state of a user may be learned according to user behavior, physical conditions of the user, activities of daily living (ADL) and associated context of daily living (CDL) of the user, or a combination thereof. One or more applications, one or more application components, one or more internet of things (IoT) devices, or a combination thereof may be identified and recommended to minimize one or more possible negative impacts upon the health state of the user.

In one aspect, the present invention provides for an open, generic, and personalized health assistant system (e.g., a cognitive system) that may monitor and mitigate a health state of a user in various activities and contexts. The present invention recommends, connects, manages, and operates an extensible set of health state monitoring and mitigation application plugins (e.g., skills), both proprietary and third-party, suited to various health conditions (e.g., diabetes, epilepsy, angina, etc.) and activities (e.g., driving, exercising, sleeping), and optionally requiring one or a variety of health monitoring devices (e.g., heartrate monitor, glucose monitor, etc.). The present invention may be omnipresent (e.g., at home, in a car, outdoors, etc.), and may activate the appropriate health applications, plugins and devices depending on the user activity and location. The present invention may be authorized to connect to one or more IoT devices in the user's environment and to issue commands to control those IoT devices in case of emergency (e.g., instruct vehicle automatic pilot to take over and safely stop the vehicle in case the driver is about to faint, or switch on an air humidifier as needed while the user is sleeping).

In one aspect, the present invention provides for a plugin-based architecture that allows dedicated health application plugins and devices to be plugged and unplugged on-demand. A recommender system recommends suitable devices and plugins depending on the user conditions, activities, and/or context. The system allows the devices and plugins to share their data to better monitor and mitigate the health state of the user.

It should be noted that as used herein, "user activity" may refer to physical activities of a user, such as driving, exercising, travelling, walking, sleeping, etc. "User health conditions" may be parameters that may indicate a presence/absence, type, and/or degree of a chronic or acute disease (e.g., diabetes, epilepsy, angina, etc.), symptom (e.g., headache, faint, etc.), history of medications/prescriptions, age, etc. A "user health state" may be a health state of an individual that may include the presence or absence of one or more conditions, symptoms or any particular variable which can help determine well-being. The user health state may include physical, mental, and/or social well-being. "User Physical Data" may be data quantifying or qualifying the physical conditions of a user such as, for example, amount of glucose, heart rate, skin temperature, etc. "User behavioral parameters" may be parameters characterizing the behavior of a user, such as driving aggressiveness, slow reaction time, walking speed, posture, etc.

"User Perception" may be a user perception of comfort and/or discomfort such as, for example, perception of pain, fatigue, self-efficacy, etc. The user perception type of data may be provided by the user. "Health device" may be an instrument (e.g., computing hardware and associated/embedded application/software) that monitors a user's physical conditions, such as a glucose monitoring watch, a heart rate monitor, a skin temperature sensor, a sleep monitor, etc. The "environment" may be a place where a user activity is taking place (e.g., vehicle, hospital, gym, outdoors, etc.). "Context" may refer to any information about external conditions related to the environment where the user is performing the activity (e.g., time of the day, temperature, humidity, season, etc.). The term "ontology" may be to be understood in its broadest sense. An ontology may include anything that can be modeled as an ontology, including but not limited to, taxonomies, thesauri, vocabularies, dictionaries, and the like (e.g., unified medical language system "UMLS" Meta-Thesaurus and Semantic Network).

Thus, in one aspect, the present invention provides for a generic, intelligent personalized health assistant suitable for a wide range of users, health conditions, activities, health devices, and environments, while remaining personalized. The present invention recommends the appropriate combinations of application/software plugins and devices based on the user conditions, activity, behavior, and available plugins and devices. The present invention may also recommend ways to improve the application/software plugins and devices, by coupling the application/software plugins and devices with others or by suggesting upgrades to the application/software plugins and devices (e.g., consider using a more accurate blood glucose monitoring device then the current one). In one aspect, in computing, a plug-in (or plugin, add-in, addin, add-on, addon, or extension) may be a software component that adds a specific feature to an existing computer program. When a program supports plug-ins, it enables customization. The plugin may be implemented in software, hardware, or a combination thereof.

For example, consider the following two scenarios. In scenario 1, an intelligent, personalized health recommendation service may be deployed in a cloud computing environment with a client application installed in a vehicle (e.g., and/or on a tablet or smartphone), which has access to the driving parameters (e.g., global positioning satellite "GPS" position, speed, acceleration, etc.). In an initial setup phase, a user (driver) may be suffering from an acute hyperthyroidism, which is a condition that may endanger the safety of the driver. In a most recent blood sample, the driver's thyroid stimulating hormone (TSH) levels were considered to be too high. The intelligent, personalized health recommendation service may be made aware of this situation either by the user and/or alternatively by a connected device or database where the user's blood sample analysis results are stored. Based on the above condition and on other users' experiences, the intelligent, personalized health recommendation service may search for suitable applications plugins and monitoring devices. The intelligent, personalized health recommendation service may identify at least two options, for example. In option 1, a hyperthyroidism plugin, from vendor X, suitable for driving and which requires a heartrate monitor may be identified. In option 2, a hyperthyroidism plugin, from vendor Y, also suitable for driving, but which requires a camera to detect fatigue from eye movement, may be identified. Since, from an earlier identification operation, the driver already has a suitable heartrate monitor connected to the intelligent, personalized health recommendation service, the intelligent, personalized health recommendation service may recommend option 1 in conjunction with the already-connected heartrate monitor. Finally, the user may accept to acquire and activate the hyperthyroidism plugin in conjunction with the already-existing heartrate monitor. The user may alternatively select or request an additional option.

In scenario 2, the intelligent, personalized health recommendation service (e.g., a health assistant) may provide a monitoring and mitigation phase. In one aspect, a heartrate monitor and the hyperthyroidism plugin may now be connected to the health assistant. The heartrate device may collect heartrate data and shares the data with the intelligent, personalized health recommendation service components, including the hyperthyroidism plugin. The hyperthyroidism application plugin observes variations in the driver's heartbeat. The hyperthyroidism application plugin further observes that variations in the heartbeat start to happen after aggressive accelerations (but were not observed at the beginning of the journey). The hyperthyroidism application plugin may recommend a combination of mitigation actions.

For example, if the detected heartbeat variations are minor: the first mitigation measures may be: (i) suggest a route with less dense traffic, (ii) suggest a route that is known to cause less stress in the driver behavior. If no improvement is visible (e.g., the detected heartbeat variations are consistent and/or worsen), a more severe mitigation solution may be provided/suggested. Examples of mitigation solutions may be: (i) drive to a nearest public transport station where the user may park and ride, and/or (ii) stop driving and pull on to the side of the road if possible.

In one aspect, cognitively reasoning and interacting may be performed with the user for collecting the feedback information, and the feedback information may be acquired using one or more IoT devices during the cognitive reasoning and interaction with the user.

A machine learning mechanism, employing one or more predictive models, may use the feedback information to learn the health state. In one aspect, the health state may include at least one or more medical conditions, a well-being (e.g., subjective well-being "SWB", emotional well-being, mental well-being, physical well-being, or an overall well-being) of the user, an emotional state of the user, biometric data, behavior patterns, a health profile of the user, or a combination thereof. In one aspect, well-being may be generally described as a normal/standardized or satisfactory condition of existence of the user or a state characterized by health, happiness, emotional stability, mental stability, physical stability, or success. A well-being of a user/patient may be defined. For example, a knowledge base or ontology may be used to define a well-being for a user/patient and may include defining and/or indicating one or more correlations between a health state, a plurality of states, medical conditions, ADL, and context of daily living (CDL). In an additional aspect, well-being may include the alleviation of adverse impacts upon a person's medical condition, emotional stability, mental stability, physical stability, financial stability, physiological problems, as well as to improve performance in many aspects of life such as daily activities, physical, emotional, mental activities, environmental conditions, and other functions, and also to contribute to the regulation of the various physiological systems of the organism (e.g., person) such as, the immune system. In one aspect, the well-being may be a subjective well-being (SWB) that may be defined as the degree to which people have positive thoughts and feelings about their lives and are often measured through self-reports of life satisfaction. A rating or scaling system may be used. For example, a number system from 1-10 may be used where 10 may indicate the greatest degree of positive thoughts and feelings while a 1 may indicate the least most degree of positive thoughts and feelings. A well-being of a person may be defined, stored, and/or included in a knowledge domain or ontology.

In one aspect, the one or more customized communications further include providing one or more notifications or suggestions to alter current activities of daily living (ADL) of the user, future ADLs of the user, or a combination thereof. As used herein, activities of daily living ("ADL" or "ADLs") may refer to any activities that people perform during a day or other time period. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADL may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A knowledge domain may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. The machine learning may provide a predictive model that may analyze, determine, identify, and/or predict any ADL behavior or activity for the user.

In one aspect, feedback information about the user may be collected from one or more IoT devices or sensors such as, for example, smart phones, wearable devices or sensors (e.g., proximity sensors, cameras, radio frequency identification "RFID" readers, biometric sensors, wearable sensors, and the like.). A stream of feedback data may be processed and the real-time flux of information enables the generation of knowledge or knowledge domain/ontology and enables the learning a health state of a user and generating personalized advice (e.g., suggestions, warnings, alerts, or recommendations) relating to the learned health state for adjusting one or more ADLs, CDLs, or other activities and environments that may negatively impact the person's well-being or state of health, using cloud computing and/or edge computing technology.

Also, as used herein, sensors may include proximity sensors, cameras, radio frequency identification "RFID" readers, biometric sensors, wearable sensors, computers, handheld devices (e.g., Global Positioning System "GPS" device or step counters), smart phones, and/or other sensor based devices.

Accordingly, the "health state" of a particular user may depend greatly upon contextual factors, such as a correlation or relationship between the health state and ADLs/CDLs of the user, and other contextual factors such as defined by a user or learned via artificial intelligence. A deeper, cognitive analysis of the health state of a person (e.g., a patient) may be learned based on, for example, standards, rules, practices, and/or learned ADLs, CDLs, and/or other related behaviors or activities. In short, a cognitive learning process using artificial intelligence may learn each of the actions, decisions, ADLs, CDLs, modes of travel, behavior patterns of a user, a medical profile (which may include data relating to medical care or medical conditions), or other activities. Each learned health state may be saved as part of a user profile and/or retained in a knowledge domain. For example, the cognitive learning may learn preferred ADLs for particular priorities (e.g., brush teeth before leaving to work), preferences (dining at a particular restaurant), or even time periods (e.g., walking to work on warm, sunny days while taking a cab to work on rainy days).

The ontology may include, but is not limited to, the knowledge domain or data repository of a collection of material, information, content and/or other resources related to a particular subject or subjects. For example, the ontology may include, data relating to a user's health state. The ontology may have defined ADLs, CDLs, and a user profile (e.g., calendar information, historical data relating to medical conditions of the user, emotional/physical/mental condition of the user, preferences, priorities, biomedical data, psychophysical parameters of the user, medical history, emotional data, skills set, and the like). The ontology may also have environmental data, traffic data, routes, roads, streets, highways, interstates, trails, bridges, maps, airports, geographical data, medical conditions, nutritional data, weather data, and the like.

One or more machine learning models may be invoked and applied to cognitive learning about the user and/or a health state such as, for example, ADLs, CDLs, priorities, activity preferences, daily or future calendaring, behaviors, skill sets of a user, medical conditions, capabilities, performance capabilities, and/or other types of data needed for providing communications to suggest one or more alterations, adjustments, or planning alternative activities to eliminate or reduce possible adverse impacts on the person's health state.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
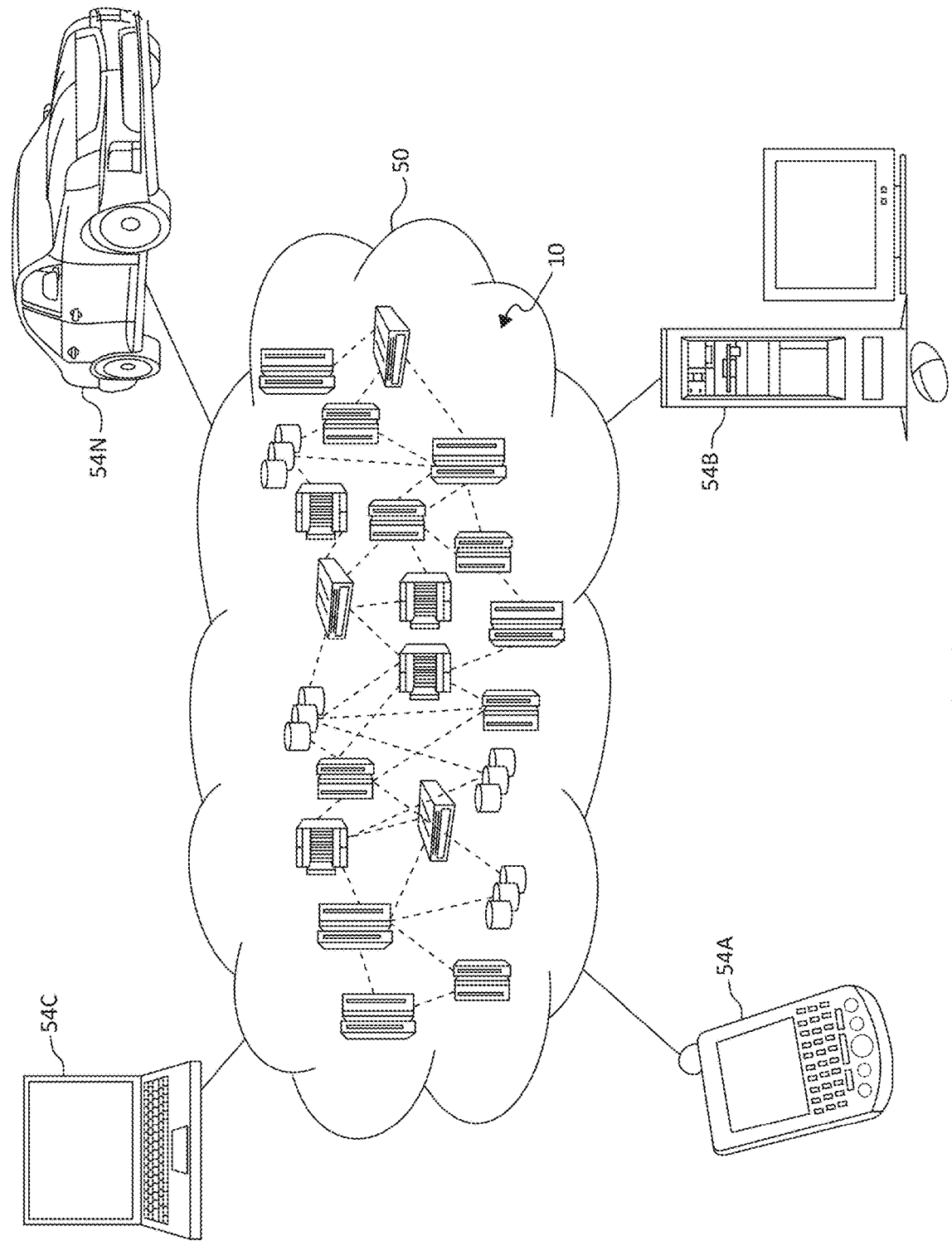
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
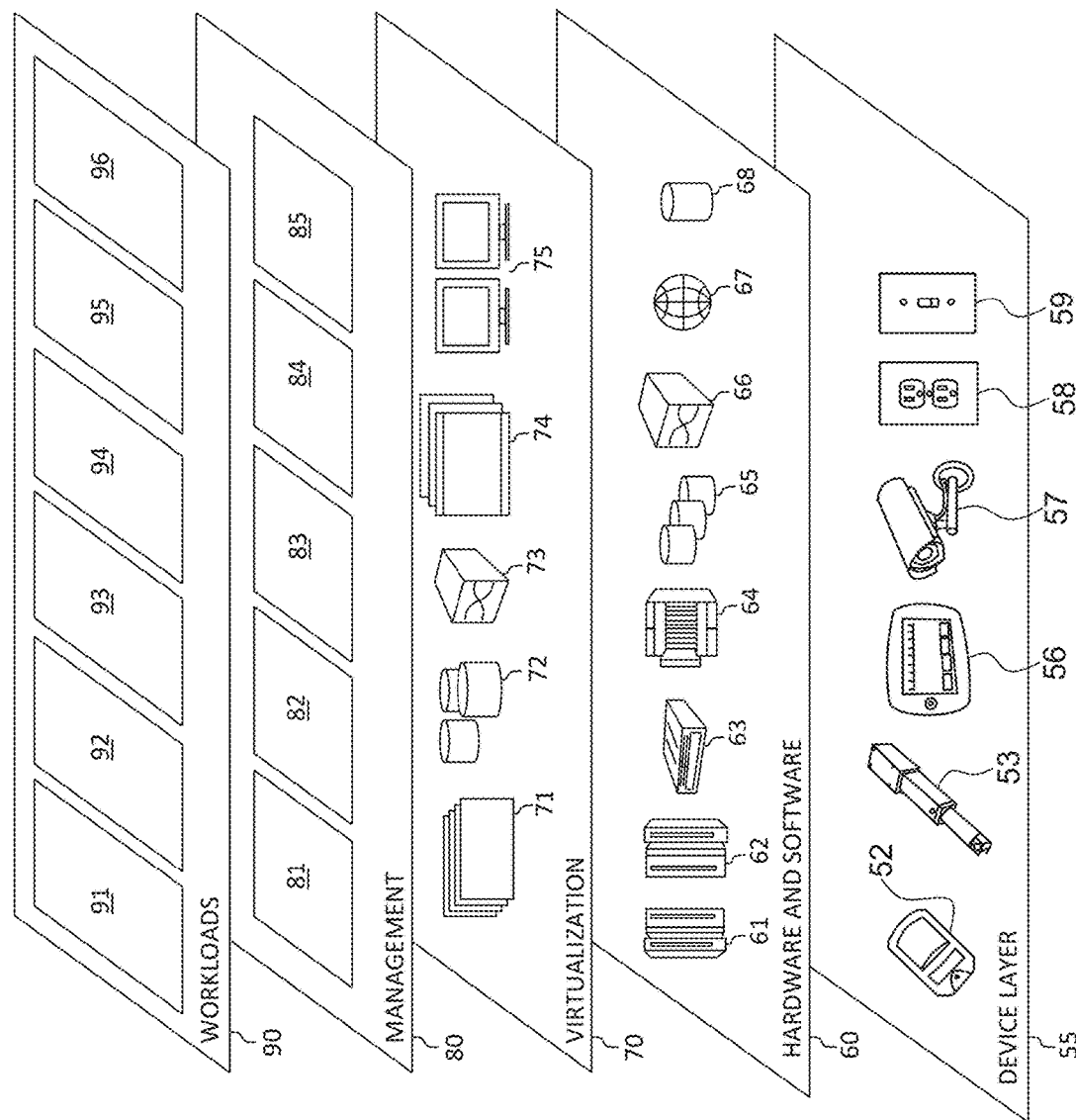
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various intelligent health recommendation service workloads and functions 96. In addition, intelligent health recommendation service workloads and functions 96 may include such operations as data analytics, data analysis, and as will be further described, notification functionality. One of ordinary skill in the art will appreciate that the intelligent health recommendation service workloads and functions 96 may also work in conjunction with other portions of the various abstraction layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for providing personalized and intelligent health recommendation services in a computing environment. The present invention may connect and provide an extensible set of health state monitoring and mitigation application/software plugins (both proprietary and third-party) suited to various health conditions (e.g., diabetes, epilepsy, angina, etc.), and optionally requiring one of a variety of health monitoring devices/data. The present invention (e.g., a cognitive health assistant system) may recommend to the user an appropriate combination of health plugins and devices depending on the user's health conditions, data, behavior, and currently available health devices (e.g., glucose monitor, sleep monitor, heart rate monitor, skin temperature monitor, etc.). One or more recommendations of health devices and application/software plugins may be learned from the experiences and feedback of multiple users.

One or more health application/software plugins, devices, and/or data may be allowed/enabled to be plugged in, replaced, or unplugged as required. The health and perception data and behavioral parameters from an extensible set of health devices, as well as from the user, may be collected. The present invention may configure and calibrate the plugins depending on the user conditions and available devices.

In an additional embodiment, the present invention may monitor and predict the user's health conditions using the connected devices and provide/make data available to the health state plugins. Data may be collected and aggregated from the health state plugins and alerting the user in case of detected or predicted state/risk. An appropriate mitigation action may be provided and/or performed (alert, instruction, machine command issued to other devices, such as vehicle, heating, etc.) as suggested by one or multiple health plugins.

The intelligent, personalized health recommendation service may perform the following steps: 1) identify and recommend, from a catalogue or collection of products, suitable/required software plugins (skills), upgrades, updates, and the required device options for the user, given his/her health conditions, activities, behavior, and perception of comfort/discomfort, 2) add/activate the health plugins and health care monitoring devices 508 on demand by the user and/or by the personal health assistant and recommender system 502 itself, 3) enabling communication and data exchange between the various system components, specifically the health plugins and health care monitoring devices, and a data analytics component, and/or 3) alerting the user about any risk and performing the mitigation actions identified by the health plugins or devices.

The present invention may select the current user activity as provided by the user or automatically, depending on the input data and active client applications, and subsequently activates the appropriate software plugins and devices. The intelligent, personalized health recommendation service, using a recommender component/system, may learn and recommend additional or alternative health software plugins depending on the user profile/conditions, group, activities, behavior, and observed data, a rule-based approach or experiences and feedback of other users.

Using one or more health software plugins, the intelligent, personalized health recommendation service may consume real-time and past data available through the device broker and from the database to assess risks related to the user conditions in the context of the current user activity and environment and may generate alerts or mitigation actions.

The intelligent, personalized health recommendation service, using the health software plugin, may support multiple devices or input parameter variants, depending on the severity or type of health conditions, which allows a for flexibility as to which device or combination of devices to use. Each health software plugin or device advertises its characteristics (usage, capabilities, input data or device options, reliability, accuracy, etc.) on the health plugin and device catalogue and marketplace.

One or more health software plugins may produce data to be shared with other components of the intelligent, personalized health recommendation service allowing further cooperation between the software plugins and devices. Each of the health software plugins may be connected to a user environment through the intelligent, personalized health recommendation service and may be authorized to perform a mitigation action in the form of machine instructions/commands to connected devices/machines (e.g., make automatic pilot take over and safely stop vehicle in case the driver is about to faint, switch on air humidifier while user is sleeping, etc.).

The intelligent, personalized health recommendation service may use a data analytics component to analyze real-time and past data, to generate additional knowledge useful/required to software plugins and/or may correlate the user perception to the user behavioral parameters, physical data, activities, and contextual parameters.

Figure 4:
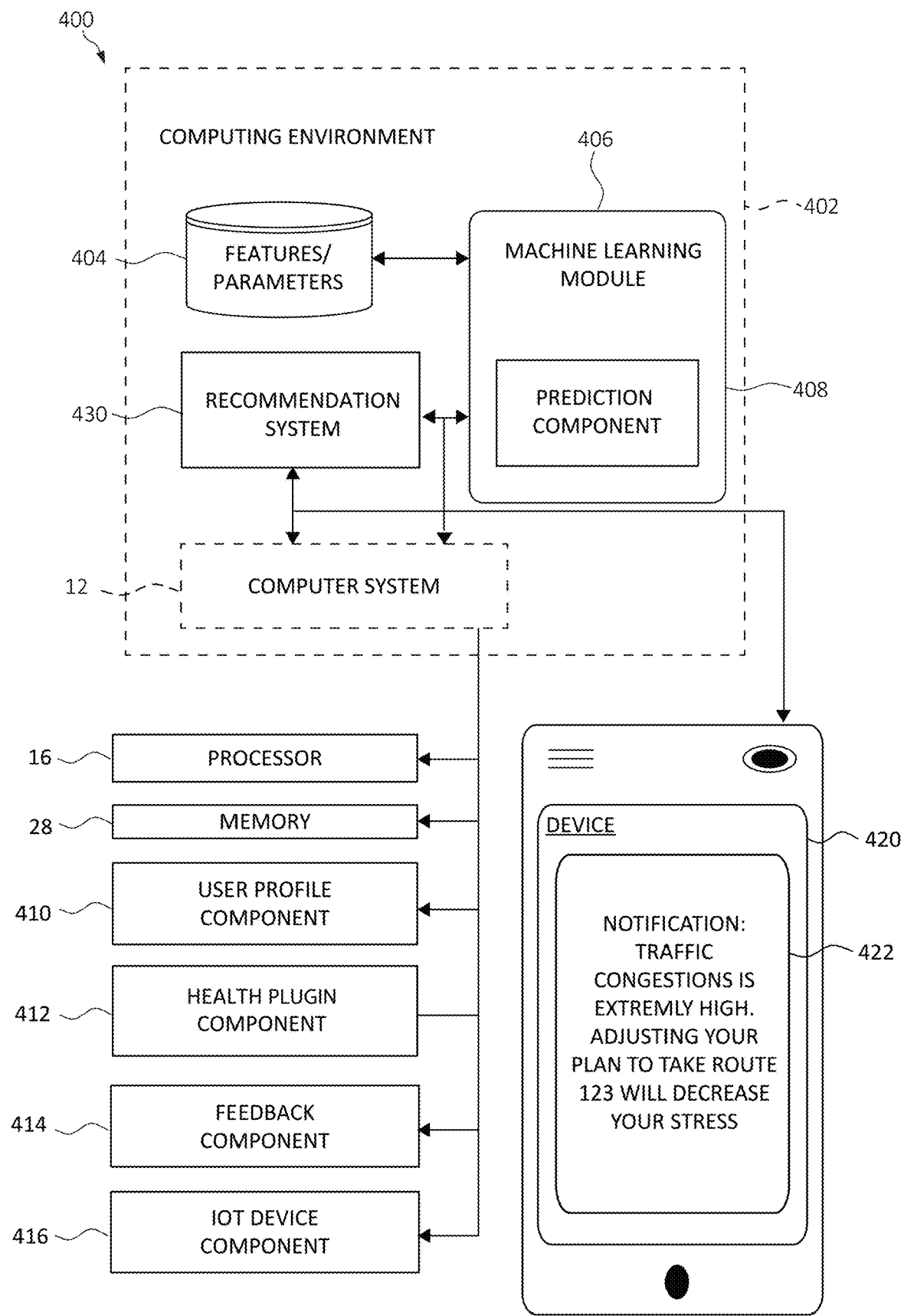
FIG. 4 is a diagram depicting various user hardware and computing components functioning in accordance with aspects of the present invention.

Turning now to FIG. 4, a block diagram depicting exemplary functional components 400 according to various mechanisms of the illustrated embodiments is shown. FIG. 4 illustrates intelligent health recommendation service workloads and functions and training of a machine-learning model in a computing environment, such as a computing environment 402, according to an example of the present technology. As will be seen, many of the functional blocks may also be considered "modules" or "components" of functionality, in the same descriptive sense as has been previously described in FIGS. 1-3. With the foregoing in mind, the module/component blocks 400 may also be incorporated into various hardware and software components of a system for implementing an intelligent health recommendation service in accordance with the present invention. Many of the functional blocks 400 may execute as background processes on various components, either in distributed computing components, or on the user device, or elsewhere. Computer system/server 12 is again shown, incorporating processing unit 16 and memory 28 to perform various computational, data processing and other functionality in accordance with various aspects of the present invention.

The system 400 may include the computing environment 402, a recommendation system 430, and a user equipment ("UE") 420, such as a desktop computer, laptop computer, tablet, smart phone, and/or another electronic device that may have one or more processors and memory. The UE 420, the recommendation system 430, and the computing environment 402 may each be associated with and/or in communication with each other, by one or more communication methods, such as a computing network. In one example, the UE 420 and/or the recommendation system 430 may be controlled by a user, an owner, customer, patient, health care provider, or administrator associated with the computing environment 402. In another example, the UE 420 and/or the recommendation system 430 may be completely independent from the user, owner, customer, patient, health care provider, or administrator of the computing environment 402. In one aspect, one or more components of computing environment 402 may be internal to the UE 420. In an alternative embodiment, one or more components of the computing environment 402 may be external to the UE 420.

In one aspect, the computing environment 402 may provide virtualized computing services (i.e., virtualized computing, virtualized storage, virtualized networking, etc.) to devices 420. More specifically, the computing environment 402 may provide virtualized computing, virtualized storage, virtualized networking and other virtualized services that are executing on a hardware substrate.

As depicted in FIG. 4, the computing environment 402 may include a machine learning module 406, features and/or parameters 404 that are associated with a machine learning module 406, and the recommendation system 430. The features and/or parameters may include ADLs, CDLs, health state data, and a knowledge domain/ontology. The features and/or parameters database 404 may also include user profiles (e.g., a collection of user profiles) for the recommendation system 430 and/or IoT devices associated with an IoT device component 416 (e.g., an IoT sensor device, camera, voice activated device, and other types of IoT devices).

It should be noted that one or more IoT devices may be represented as the IoT device component 416 may be coupled to the recommendation system 430. The features and/or parameters 404 may be a combination of ADLs, CDLs, features, parameters, rules, behavior characteristics, biometric data, user profile data, calendaring data, health and nutrition data, physical or mental capabilities, emotional data, medical condition data, nutritional constraint data, health constraint data, historical data, tested and validated data, or other specified/defined data for testing, monitoring, validating, detecting, learning, analyzing and/or calculating various conditions or diagnostics relating to cognitively learning the health state of a user for identifying and recommending one or more applications, one or more application components (e.g., plugins), one or more internet of things (IoT) devices, or a combination thereof to minimize one or more possible negative impacts upon the health state of the user and/or to avoid adverse impacts on the user's health state in the recommendation system 430.

That is, different combinations of ADLs, CDLs, features, or parameters may be selected and applied to the input data for learning or training one or more machine learning models of the machine learning module 406. The features and/or parameters 404 may define one or more settings of an IoT device (e.g., UE 420) associated with the IoT device component 416 to enable the UE 420 to interact with a member or user of the UE 420 and the computer system 12. The IoT device component 416 may be associated with the recommendation system 430 and the UE 420.

The computing environment 402 may also include the computer system 12, as depicted in FIG. 1. The computer system 12 may also include the user profile component 410, a health plugin component 412, a feedback component 414, and the IoT device component 416 each associated with the machine learning module for training and learning one or more machine learning models and also for applying multiple combinations of ADLs, CDLs, features, parameters, behavior patterns or characteristics, patient/user profile data, historical data, or a combination thereof to the machine learning model for use in the recommendation system 430 for cognitively learning a health state of a user and for identifying and recommending one or more applications, one or more application components (e.g., plugins), one or more internet of things (IoT) devices, or a combination thereof to minimize one or more possible negative impacts upon the health state of the user and/or to avoid adverse impacts on the user's health state.

In one aspect, the machine learning module 406, which may be associated with the recommendation system 430, may include a prediction component 408 for cognitively learning a health state of a user and recommending personalized advice, suggestions, or notifications of a user/patient profile using one or more recommended applications, application components (e.g., plugins), and/or IoT devices, or a combination thereof to minimize one or more possible negative impacts upon the health state of the user and/or to avoid adverse impacts on the user's health state, by one or more IoT devices 420 associated with the IoT device component 416 in the recommendation system 430.

The user profile component 410 may include data relating to a health state of a user (e.g., the well-being of the user), ADLs, CDLs, behavioral patterns and characteristics, biometric data, medial history data, contextual data, feedback information, and data associated with the knowledge domain/ontology.

The computer system 12 may use the user profile component 410 to cognitively determine the level of the well-being or health state of the user according to user behavior, physical conditions of the user, ADLs and associated CDLs of the user, or a combination thereof. The user profile component 410 may collect, gather, calculate, and cognitively determine the well-being/health state. The user profile component 410 may monitor the health state of the user using the one or more applications, the one or more application components, the one or more IoT devices, or a combination thereof. The user profile component 410 may also cognitively determine the well-being/health state via the identified and/or recommended applications, application components, one or more IoT devices, or a combination thereof.

Also, the recommendation system 430 may recommends one or more devices (e.g., UE 420) and/or software components such as, for example, one or more health plugins (via health plugin component 412).

The health plugin component 412 may identify and recommend one or more applications, one or more application components, one or more IoT devices, or a combination thereof to minimize one or more possible negative impacts upon the health state of the user.

The IoT device component 416 may provide an indication/message to an IoT device such as, for example UE 42 to activate, deactivate, or configure the one or more applications, one or more application components, one or more IoT devices, or a combination thereof to monitor the health state of the user.

The health plugin component 412 may also provide an indication/message to a health plugin such as, for example, a health plugin of UE 420 to aggregate data from the one or more applications, the one or more application components, one or more IoT devices (e.g., UE 420), or a combination thereof according to identify the one or more health state risks. Thus, the health plugin component 412 may recommend one or more mitigation actions (e.g., recommend one or more mitigating actions to avoid one or more possible negative impacts upon the health state of the user according to the aggregated data) while the recommendation system 430 recommends one or more devices (e.g., UE 420) and/or software components such as, for example, one or more health plugins (via health plugin component 412).

A feedback component 414 may use a variety of feedback information relating to the recommendation system 430 and feedback information pertaining to the user may be stored and maintained in the feedback component 414 and used by the machine learning module 406, the features and/or parameters 404, or both. The feedback component 414 may collect a variety of feedback information for the user/patient. For example, the feedback component 414 may collect data gathered from the user (e.g., cognitive interaction and reasoning), a UE 420, or other source for learning health state components and IoT devices (e.g., UE 420) suitable to users depending on the health conditions, activities, and environments of the user.

The machine learning module 406, in association with the feedback component 414, may collect the feedback, learn the one or more application components, the IoT devices, or a combination thereof suitable to users depending on their health conditions, activities, and environments.

Also, the UE 420 may include a graphical user interface (GUI) 422 enabled to display on the UE 420 one or more user interface controls for a user to interact with the GUI 422. For example, the GUI 422 may display one or more customized communications to a user to alter one or more activities of the user so as to avoid one or more possible negative impacts upon the health state of the user via an interactive graphical user interface (GUI). That is, the GUI 422 may display identified and recommended applications, application components, IoT devices, or a combination thereof to minimize one or more possible negative impacts upon the health state of the user. The GUI 422 may display one or more mitigating actions to avoid one or more possible negative impacts upon the health state of the user according to the aggregated data.

For example, the one or more customized communications may indicate or display audibly and/or visually on the GUI 422 "Notification: Traffic congestion is extremely high. Adjusting your plan to take route 123 will decrease your stress." The message notification on the GUI 422 may vary, change, and be updated according to real time feedback received from the feedback component 414. Also, the message notification on the GUI 422 may be a series of interactive messages between a user of the UE 420 and the computing environment 402.

In one aspect, the machine learning module 406 may cognitively learn a health state of a user and generating recommended applications/devices, and estimation/predictive modeling (or machine learning modeling), as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perception, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the computing system 12/computing environment 402 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Figure 5:
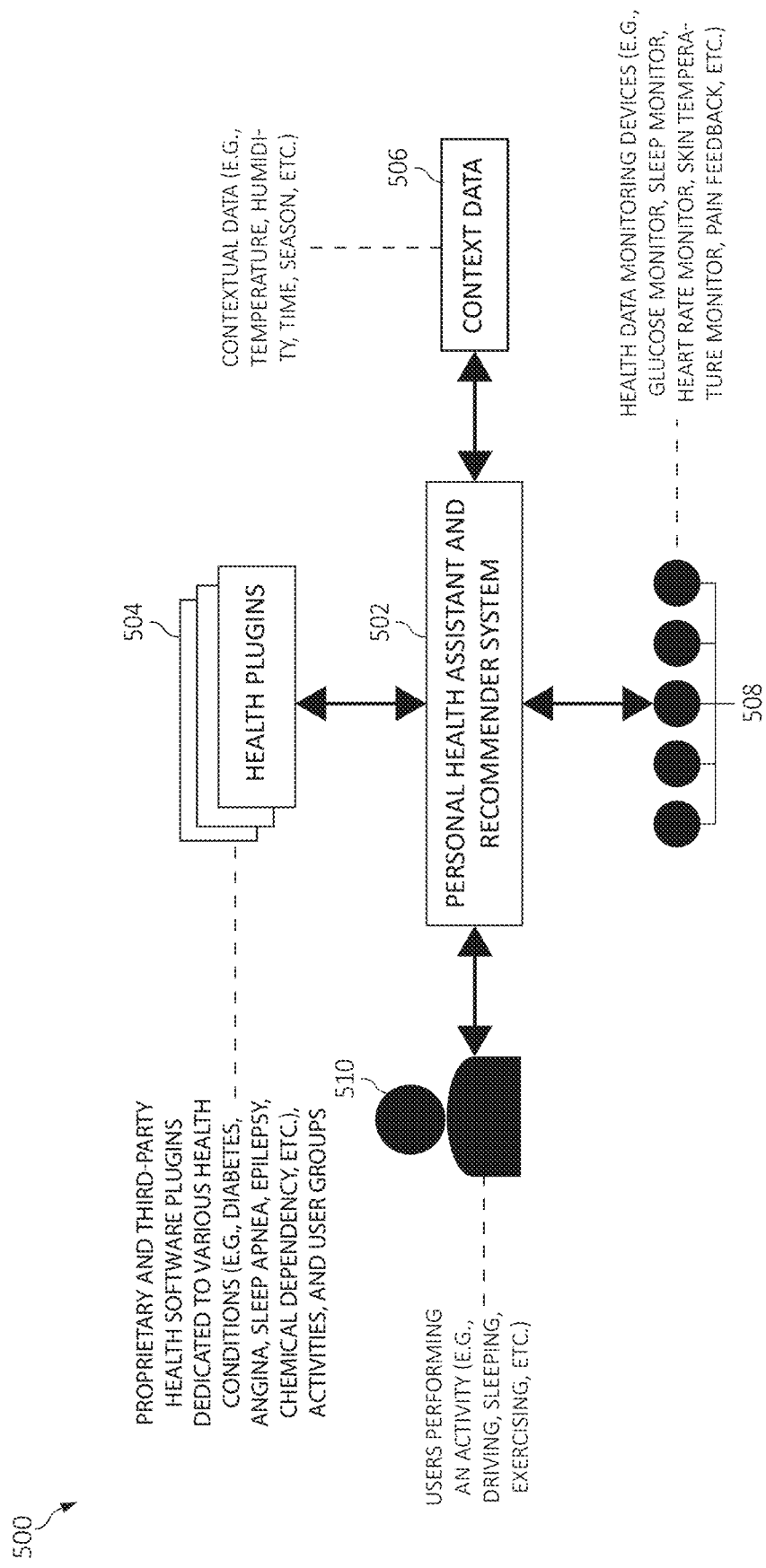
FIG. 5 is an additional block diagram depicting an exemplary functional relationship between various aspects of the present invention.

Turning now to FIG. 5, a block diagram of an exemplary functionality 500 of an intelligent health recommendation service/assistant system architecture is depicted. It should be noted that the intelligent health recommendation service/assistant system may be included in and/or associated with computer system/server 12 of FIG. 1, incorporating one or more processing unit(s) 16 to perform various computational, data processing and other functionality in accordance with various aspects of the present invention.

As shown, the various blocks of functionality are depicted with arrows designating the blocks' 500 relationships with each other and to show process flow of the cognitive health state learning and personalized advice generation system 500. Additionally, descriptive information is also seen relating each of the functional blocks 500. As will be seen, many of the functional blocks may also be considered "modules" or "components" of functionality, in the same descriptive sense as has been previously described in FIGS. 1-4. With the foregoing in mind, the module blocks 500 may also be incorporated into various hardware and software components of a system for implementing an intelligent health recommendation service/assistant in accordance with the present invention. Many of the functional blocks 500 may execute as background processes on various components, either in distributed computing components, or on the user device, or elsewhere, and generally unaware to the user performing generalized tasks of the present invention.

As illustrated in FIG. 5, a personal health assistant and recommender system 502 may identify and determine user 510 performing one or more various types of activities or "ADL" (e.g., driving, sleeping, exercising, etc.). One or more health data monitoring devices 508 may be used to collect data from user 510 and provide to the personal health assistant and recommender system 502 a health state of a user including, but not limited to, health conditions (e.g., chronic or acute diseases), symptoms, user activity, user physical data, user perception feedback, and/or user behavioral parameters.

Also, context data 506 (e.g., contextual data that may include air temperature, humidity, time, season, etc.) may be obtained from one or more alternative devices such as, for example, digital assistant (PDA) or cellular telephone 54A, desktop computer 54B, laptop computer 54C, and/or automobile computer system 54N of FIG. 2 or other external computing device. Optionally data from other users may also be collected and received as context data 506.

Using the obtained data in conjunction with the identified user activities (e.g., input data), the personal health assistant and recommender system 502 may recommend one or more health plugins 504 (e.g., an extensible set of health state monitoring and mitigation application/software plugins (both proprietary and third-party)) suited to various health conditions (e.g., diabetes, epilepsy, angina, etc.) and recommend one or more of the health monitoring devices/data 508. In one aspect, the health plugins 504 may include proprietary and third-party health application/software plugins dedicated to various health conditions (e.g., diabetes, angina, sleep apnea, epilepsy, chemical/prescription dependency (e.g., alcohol dependency), etc.), activities, and/or user groups.

That is, the personal health assistant and recommender system 502 may recommend (e.g., output) to the user 510 an appropriate combination of health plugins 504 and health care monitoring devices 508 depending on the user's health conditions, data, behavior, and currently available health devices (e.g., glucose monitor, sleep monitor, heart rate monitor, skin temperature monitor, etc.).

Thus, the personal health assistant and recommender system 502 may detect the activity type and/or location of user 510, depending on which health care monitoring devices 508 and client applications. The personal health assistant and recommender system 502 may also detect/identify context data 506. The personal health assistant and recommender system 502 may activate the health plugins 504 and health care monitoring devices 508 relevant to the user activity of user 510 and start monitoring the user health parameters and behavior.

Thus, the personal health assistant and recommender system 502 may return as output to user 510 recommendations of health software plugins (skills) and suitable devices to use/activate. Risk assessment results related to the input parameters may be provided by the personal health assistant and health plugins 504. One or more alerts and mitigation actions, depending on the user activity, may be provided.

Figure 6:
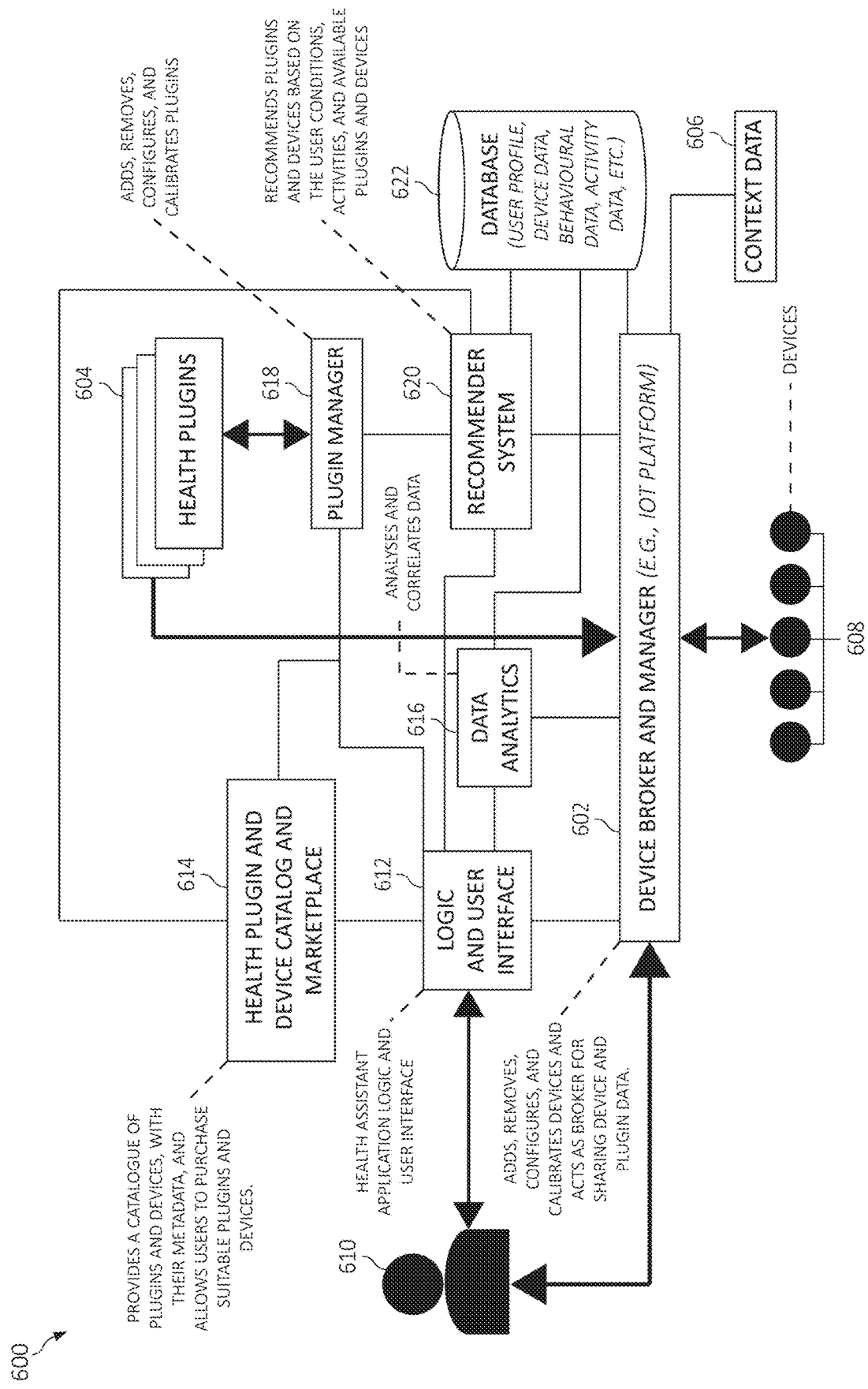
FIG. 6 is an additional block diagram depicting an exemplary functional relationship between various aspects of the present invention.

Turning now to FIG. 6, a block diagram of exemplary functionality of an intelligent health recommendation service/assistant system 600 is depicted. It should be noted that the intelligent health recommendation service/assistant system may be included in and/or associated with computer system/server 12 of FIG. 1, incorporating one or more processing unit(s) 16 to perform various computational, data processing and other functionality in accordance with various aspects of the present invention.

As shown, the various blocks of functionality are depicted with arrows designating the blocks relationships with each other and to show process flow of the intelligent health recommendation service/assistant system 600. Additionally, descriptive information is also seen relating each of the functional blocks of intelligent health recommendation service/assistant system 600. As will be seen, many of the functional blocks may also be considered "modules" or "components" of functionality, in the same descriptive sense as has been previously described in FIGS. 1-5. With the foregoing in mind, the module/component blocks of intelligent health recommendation service/assistant system 600 may also be incorporated into various hardware and software components of a system for implementing an intelligent health recommendation service/assistant in accordance with the present invention.

The intelligent health recommendation service/assistant system 600 may include a device broker and manager 602, one or more health plugins 604, devices 608, a logic and user interface 612 ("UI"), a health plugin and device catalog and marketplace 614, a data analytics component 616 (e.g., "data analytics"), a plugin manager 618, a recommender system 620, a database 622, each of which may be in communication with each other and also in communication with user 610 and context data 606 (e.g., context data from one or more alternative devices).

In one aspect, the one or more health plugins 604 may be health state/risk monitoring and mitigation applications that may be connected to the device broker and manager 602. The health plugins 604 may be considered as skills. Each of the one or more health plugins 604 may be dedicated to specific health conditions (e.g., diabetes, epilepsy, etc.), dedicated to one or more user groups (e.g., elderly, children, etc.), and also dedicated to one or more activities (e.g., driving, sleeping, exercising, etc.). The one or more health plugins 604 may require a variety of input data or devices. Each of the one or more health plugins 604 may advertise the features and capabilities, the required input data and device options (and required level of quality), and the types of output data. Each of the one or more health plugins 604 may consume/monitor device data and produce new data, notifications (alerts), and recommendations or instructions/commands. The data/alerts of each of the one or more health plugins 604 may then be used by the device broker and manager 602 to perform appropriate actions and used by other devices connected to the device broker and manager 602 (e.g., an IoT device).

By way of example only, the one or more health plugins 604 may include the following examples. An application plugin that combines a peak flow meter and oximeter information to check and control asthma, application plugins suitable for diabetic drivers, and which requires a glucose monitoring device, an application plugin for detecting safety-critical levels of glucose (and depending on the type of diabetes and its severity) and performing an appropriate action such as, for example, alerting the driver to stop immediately, or in the case of automated driving instructs the vehicle to stop. Also, the one or more health plugins 604 may include an application plugin that aggregates physical data from various devices and generates new/additional knowledge (data). Additionally, the one or more health plugins 604 may include an application plugin that acts as a connector for a third-party hardware device that does not support the data model of the device broker and manager 602.

The devices 608 may provide user physical data to each of the components in an intelligent health recommendation service/assistant system such as, for example, health plugins 604. Thus, the devices 608 may be connected automatically and/or on demand to one or more components in an intelligent health recommendation service/assistant system such as, for example, health plugins 604.

The devices 608 publish, communicate, and/or advertise each of the features, characteristics, input and output data, or other data intelligent health recommendation service/assistant system. The devices 608 may exchange data with the remaining components of the companion through the device broker and manager 602. One or more of the health plugins 604 may support a multitude of device type options, each leading to a different level of reliability of the outputs. The devices 608 may be a portable/handheld: device, an oximeter, a glucose monitor, a heart rate monitor, an accelerometer, a global positioning satellite ("GPS") device, a blood pressure monitor, a spirometer, a computed tomography ("CT") scanner, an X-ray, an electrocardiography ("ECK" or "ECG") device, a magnetic resonance imaging ("MRI") device, emergency education consultant devices, or other devices capable of measuring biometric or physical data associated with a user.

The plugin manager 618 enables the intelligent health recommendation service/assistant system 600 to add (install), configure, calibrate, activate/deactivate, and remove one or more health plugins 604 on demand and/or automatically in real-time.

The device broker and manager 602 allows the intelligent health recommendation service/assistant system 600 to manage devices 608 and to exchange data between the components (e.g., devices 608, health plugins 604, and the data analytics component 616) of the intelligent health recommendation service/assistant system 600.

The recommender system 620 may suggest one or more health plugins 604 and devices 608 to users, based on the profile of the users (e.g., user 610), health conditions, user activities, and already available plugins and devices (e.g., devices 608, health plugins 604, etc.). The recommender system 620 may use a machine learning operation in conjunction with data from other users (e.g., similar user profiles) such as, for example, feedback data from other users. The recommender system 620 may recommend one or more health plugins 604 suitable for the user's health conditions and activities and may recommend one or more devices 608. The recommender system 620 may recommend a suitable health device (e.g., one or more devices 608) for one or more health plugins 604, depending on the user's health conditions and activities. The recommender system 620 may take into consideration user behavior, perception, or physical data to suggest new/alternative health plugins 604 or devices 608.

In one aspect, examples of a health plugin 604 may include, for example, an application for a driver with acute hyperthyroidism. The recommender system 620 may recommend installing an appropriate software plugin (e.g., one or more health plugins 604) dedicated to the acute hyperthyroidism health condition and suitable for driving, along with a compatible heartrate monitor and/or fatigue detection camera/component of devices 608.

The data analytics component 616 analyzes and correlates data exchanged through the device broker and manager 602. The data analytics component 616 extracts additional knowledge from the available data such as, for example, statistics about user health data, extract correlations between observed health data, and user behavior and feedback such as, for example, perception of pain, comfort, etc. The data analytics component 616 shares the data (e.g., outputs) with the remaining system components of the intelligent health recommendation service/assistant system 600 through the device broker and manager 602.

In one aspect, the heath plugin and device catalog and marketplace 614 may provide a catalog of plugins and devices, with associated metadata, and enable a user to access and/or purchase suitable plugins and devices. That is, the heath plugin and device catalog and marketplace 614, which makes available the one or more health plugins proprietary and third-party health plugins and devices. The marketplace includes the necessary plugin and device metadata allowing the plugin manager and device manager to automatically install, configure, calibrate, and remove health plugins and devices.

Figure 7:
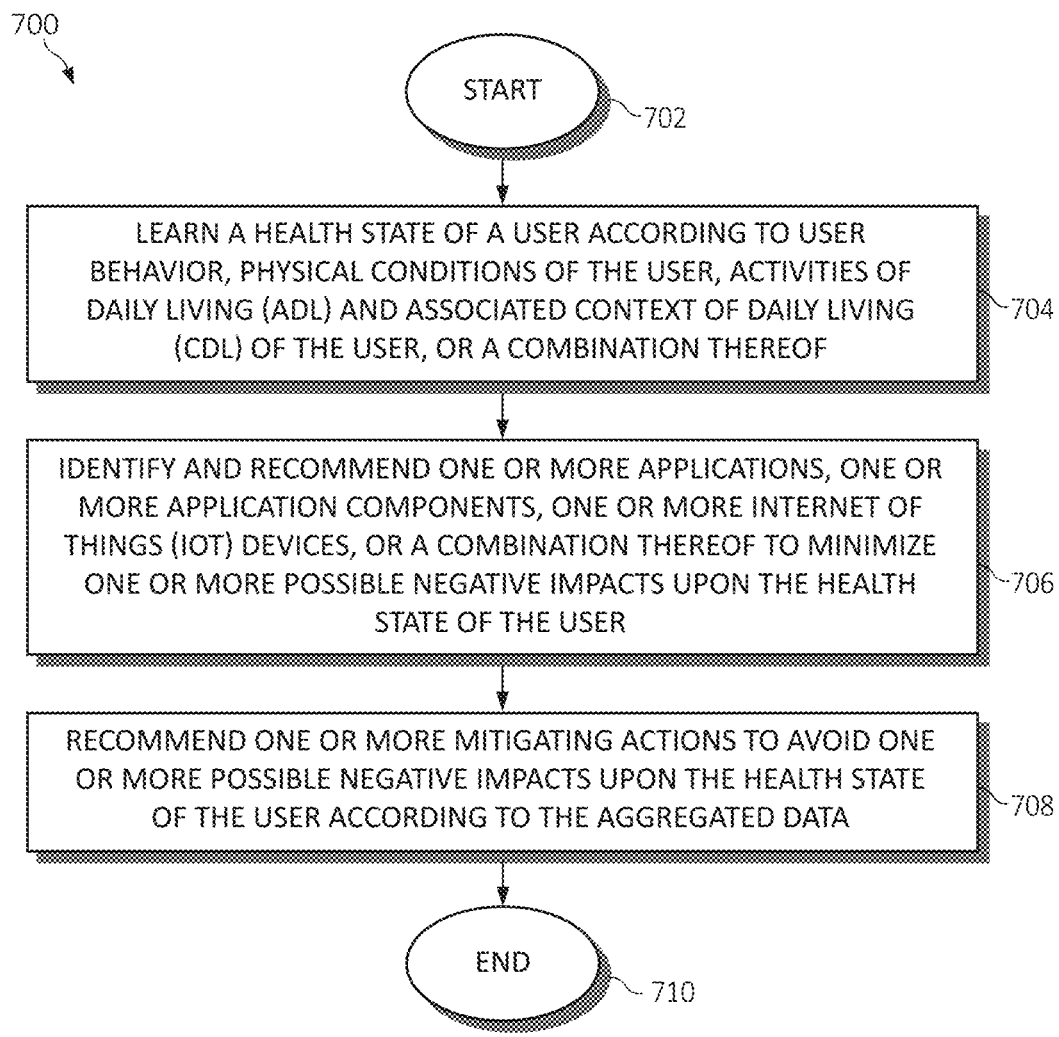
FIG. 7 is a flowchart diagram depicting an exemplary method for implementing an intelligent health recommendation service by a processor, again in which aspects of the present invention may be realized.

Turning now to FIG. 7, a method 700 for implementing an intelligent health recommendation service by a processor is depicted, in which various aspects of the illustrated embodiments may be implemented. The functionality 700 may be implemented as a method executed as instructions on a machine, where the instructions are included on at least one computer readable medium or one non-transitory machine-readable storage medium. The functionality 700 may start in block 702.

A health state of a user may be learned according to user behavior, physical conditions of the user, ADLs and associated CDLs of the user, or a combination thereof, as in block 704. One or more applications, one or more application components, one or more internet of things (IoT) devices, or a combination thereof may be identified and recommended to minimize one or more possible negative impacts upon the health state of the user, as in block 706. One or more mitigating actions may be recommended to avoid one or more possible negative impacts upon the health state of the user according to the aggregated data, as in block 708. The functionality 700 may end, as in block 710.

In one aspect, in conjunction with and/or as part of at least one block of FIG. 7, the operations of method 700 may include each of the following. The operations of method 700 may activate, deactivate, or configure the one or more applications, one or more application components, one or more internet of things (IoT) devices, or a combination thereof to monitor the health state of the user. The operations of method 700 may monitor the health state of the user using the one or more applications, the one or more application components, the one or more IoT devices, or a combination thereof. The operations of method 700 may recommend one or more mitigating actions to avoid one or more possible negative impacts upon the health state of the user according to the collected data, the one or more application components, the one or more IoT devices, or a combination thereof.

The operations of method 700 may aggregate data from the one or more applications, the one or more application components, the IoT devices, or a combination thereof according to identify the one or more health state risks, recommend one or more mitigating actions to avoid one or more possible negative impacts upon the health state of the user according to the aggregated data, and/or predict a health state of a user according to aggregating data collected from the one or more applications, the one or more application components, the IoT devices, or a combination thereof according to identify the one or more health state risks. That is, the machine learning mechanism may be initialized to collect feedback, learn one or more combinations of health plugins and the one or more IoT devices for the user according to health conditions, activity, and environment of the user. A machine learning mechanism may be initialized to collect feedback, learn the health state of the user, learn one or more mitigating actions, or a combination thereof, wherein the health state includes at least one or more medical conditions, a subjective well-being (SWB) of the user, an emotional state of the user, biometric data, behavior patterns, a health profile of the user, or a combination thereof.

Moreover, the operations of method 700 may implement a set of rules for using a predictive model. The feedback information, a health state profile of the user, one or more ADLs of the user, CDLs, or a combination thereof may be used in the predictive model. The user feedback may also be augmented with information from a knowledge domain that describes correlations between the health state, ADL, CDL, or a combination thereof of the user.

The operations of method 700 may adjust future customized applications, the one or more application components, the IoT devices, or a combination thereof according to updated feedback information, adjust one or more ADLs, one or more CDLs, or a combination thereof based on the customized communications.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for implementing an intelligent health recommendation service by a processor, comprising:
   recursively gathering and analyzing data from one or more Internet of things (IoT) devices;
   learning a health state of a user according to user behavior, physical conditions of the user, activities of daily living (ADL) and associated context of daily living (CDL) of the user, or a combination thereof, wherein the learning is performed by executing machine learning logic to train one or more machine learning models using the data inputs recursively gathered and analyzed from the one or more IoT devices; and
   identifying and recommending one or more applications, one or more application components, and any of the one or more of the IoT devices necessitated by the one or more applications applicable to an automatically identified specific health condition of the user, based on the learned health state of the user, to minimize one or more possible negative impacts upon the health state of the user, wherein the one or more application components are extensible plug-ins to the one or more applications activated and deactivated in real-time according to contextual information of a current activity of the user, and wherein the recommendation facilitates a decision by the user with respect to utilization and implementation of the one or more applications, one or more application components, one or more IoT devices, or combination thereof.

2. The method of claim 1, further including configuring the one or more applications, one or more application components, the one or more IoT devices, or a combination thereof to monitor the health state of the user according to the current activity of the user.

3. The method of claim 1, further including monitoring the health state of the user using the one or more applications, the one or more application components, the one or more IoT devices, or a combination thereof.

4. The method of claim 1, further including aggregating data from the one or more applications, the one or more application components, the one or more IoT devices, or a combination thereof to identify the one or more health state risks.

5. The method of claim 4, further including recommending one or more mitigating actions to avoid one or more possible negative impacts upon the health state of the user according to the collected data, the one or more application components, the one or more IoT devices, or a combination thereof.

6. The method of claim 1, further including predicting the health state of the user according to aggregating data collected from the one or more applications, the one or more application components, the one or more IoT devices, or a combination thereof according to identify the one or more health state risks.

7. The method of claim 1, further including initializing a machine learning mechanism to collect feedback, learn one or more combinations of health plugins and the one or more IoT devices for the user according to health conditions, activity, and environment of the user.

8. A system for implementing an intelligent health recommendation service, comprising:
one or more computers with executable instructions that when executed cause the system to:
recursively gather and analyze data from one or more Internet of things (IoT) devices;
learn a health state of a user according to user behavior, physical conditions of the user, activities of daily living (ADL) and associated context of daily living (CDL) of the user, or a combination thereof, wherein the learning is performed by executing machine learning logic to train one or more machine learning models using the data inputs recursively gathered and analyzed from the one or more IoT devices; and
identify and recommend one or more applications, one or more application components, and any of the one or more of the IoT devices necessitated by the one or more applications applicable to an automatically identified specific health condition of the user, based on the learned health state of the user, to minimize one or more possible negative impacts upon the health state of the user, wherein the one or more application components are extensible plug-ins to the one or more applications activated and deactivated in real-time according to contextual information of a current activity of the user, and wherein the recommendation facilitates a decision by the user with respect to utilization and implementation of the one or more applications, one or more application components, one or more IoT devices, or combination thereof.

9. The system of claim 8, wherein the executable instructions further configure the one or more applications, one or more application components, the one or more IoT devices, or a combination thereof to monitor the health state of the user according to the current activity of the user.

10. The system of claim 8, wherein the executable instructions further monitor the health state of the user using the one or more applications, the one or more application components, the one or more IoT devices, or a combination thereof.

11. The system of claim 8, wherein the executable instructions further aggregate data from the one or more applications, the one or more application components, the one or more IoT devices, or a combination thereof to identify the one or more health state risks.

12. The system of claim 11, wherein the executable instructions further recommend one or more mitigating actions to avoid one or more possible negative impacts upon the health state of the user according to the collected data, the one or more application components, the one or more IoT devices, or a combination thereof.

13. The system of claim 8, wherein the executable instructions further predict the health state of the user according to aggregating data collected from the one or more applications, the one or more application components, the one or more IoT devices, or a combination thereof according to identify the one or more health state risks.

14. The system of claim 8, wherein the executable instructions further initialize a machine learning mechanism to collect feedback, learn one or more combinations of health plugins and the one or more IoT devices for the user according to health conditions, activity, and environment of the user.

15. A computer program product for, by a processor, implementing an intelligent health recommendation service, the computer program product comprising a non-transitory computer-readable storage medium having computer-readable program code portions stored therein, the computer-readable program code portions comprising:
an executable portion that recursively gathers and analyzes data from one or more Internet of things (IoT) devices;
an executable portion that learns learn a health state of a user according to user behavior, physical conditions of the user, activities of daily living (ADL) and associated context of daily living (CDL) of the user, or a combination thereof, wherein the learning is performed by executing machine learning logic to train one or more machine learning models using the data inputs recursively gathered and analyzed from the one or more IoT devices; and
an executable portion that identifies and recommends one or more applications, one or more application components, and any of the one or more of the IoT devices necessitated by the one or more applications applicable to an automatically identified specific health condition of the user, based on the learned health state of the user, to minimize one or more possible negative impacts upon the health state of the user, wherein the one or more application components are extensible plug-ins to the one or more applications activated and deactivated in real-time according to contextual information of a current activity of the user, and wherein the recommendation facilitates a decision by the user with respect to utilization and implementation of the one or more applications, one or more application components, one or more IoT devices, or combination thereof.

16. The computer program product of claim 15, further including an executable portion that configures the one or more applications, one or more application components, the one or more IoT devices, or a combination thereof to monitor the health state of the user according to the current activity of the user.

17. The computer program product of claim 15, further including an executable portion that monitor the health state of the user using the one or more applications, the one or more application components, the one or more IoT devices, or a combination thereof.

18. The computer program product of claim 15, further including an executable portion that aggregates data from the one or more applications, the one or more application components, the one or more IoT devices, or a combination thereof to identify the one or more health state risks.

19. The computer program product of claim 18, further including an executable portion that:

recommends one or more mitigating actions to avoid one or more possible negative impacts upon the health state of the user according to the collected data, the one or more application components, the one or more IoT devices, or a combination thereof; or predicts the health state of the user according to aggregating data collected from the one or more applications, the one or more application components, the one or more IoT devices, or a combination thereof according to identify the one or more health state risks.

20. The computer program product of claim 15, further including an executable portion that initializes a machine learning mechanism to collect feedback, learn one or more combinations of health plugins and the one or more IoT devices for the user according to health conditions, activity, and environment of the user.

* * * * *